United States Patent [19]

Petty et al.

[11] Patent Number: 5,080,866
[45] Date of Patent: Jan. 14, 1992

[54] ANALYTIC APPPARATUS AND METHOD

[76] Inventors: John D. Petty, 34 Palm Avenue, Holland Park, 4121 Queensland; Russell M. Peachey, 36 Freeman Road, Durack, 4077, Queensland; Denis R. Sweatman, 811 Oxley Road, Corinda, 4075, Queensland, all of Australia

[21] Appl. No.: 631,179

[22] Filed: Dec. 19, 1990

Related U.S. Application Data

[63] Continuation of Ser. No. 94,734, Jul. 7, 1987, abandoned.

[30] Foreign Application Priority Data

| Nov. 7, 1985 | [AU] | Australia | PH3289 |
| Jan. 8, 1986 | [AU] | Australia | PH4133 |
| Jan. 8, 1986 | [AU] | Australia | PH4134 |
| Jan. 8, 1986 | [AU] | Australia | PH4135 |
| Jul. 18, 1986 | [AU] | Australia | PH7008 |

[51] Int. Cl.$^5$ .......................................... G01N 35/00
[52] U.S. Cl. ............................... 422/80; 422/81; 422/110; 422/116; 436/51; 436/52; 436/53; 436/54; 436/163
[58] Field of Search ............ 422/80, 81, 110, 116; 36/51-54, 163

[56] References Cited

U.S. PATENT DOCUMENTS

| 2,977,199 | 3/1961 | Quittner | 422/75 X |
| 3,186,800 | 6/1965 | Strickler | 422/76 X |
| 3,192,017 | 6/1965 | Kruger | 422/76 |
| 3,398,689 | 8/1968 | Allington . | |
| 3,668,936 | 6/1972 | Herron . | |
| 4,120,657 | 10/1978 | Nagy et al. | 422/75 X |
| 4,273,742 | 6/1981 | Huber et al. | 422/81 X |
| 4,333,356 | 6/1982 | Bartels et al. | 73/864.21 |
| 4,441,374 | 4/1984 | Suzuki | 422/81 X |
| 4,486,097 | 12/1984 | Riley | 422/82 X |
| 4,695,431 | 9/1987 | Farrell | 436/52 X |

FOREIGN PATENT DOCUMENTS

| 17858 | 8/1983 | Australia . |
| 2327543 | 10/1976 | France . |
| 2085161 | 10/1981 | United Kingdom . |
| 2112519 | 11/1982 | United Kingdom . |

Primary Examiner—Jill Johnston
Attorney, Agent, or Firm—Knobbe, Martens, Olson & Bear

[57] ABSTRACT

A method of analysis in which a first fluid is delivered to a sensing position at a controlled first rate of flow through a fluid junction. Fluid including this first fluid is pumped to the sensing position at a rate of flow greater than the first rate, whereby to aspirate further fluid into the first fluid at the fluid junction. A condition of the fluid is sensed at the sensing position. Associated analytic apparatus includes first and second pumps (1, 2). The first pump has a pair of ports and the second pump has at least one port. A conduit (4, 5) provides fluid flow communication from a first of the ports of the first pump (1) to the port of the second pump (2). A fluid junction (3) in the conduit (4, 5) is spaced from the second pump for admitting a further fluid to the conduit. A sensor (13) is associated with the conduit (5) to sense a condition of the fluid in the conduit at least at a sensing position between the fluid junction (3) and the second pump (2). The first and second pumps (1, 2) are respectively operable to deliver a first fluid to the conduit at a controllable first rate and to draw fluid from the conduit at a rate greater than this first rate, whereby to aspirate further fluid into the conduit at the fluid junction.

31 Claims, 8 Drawing Sheets

»
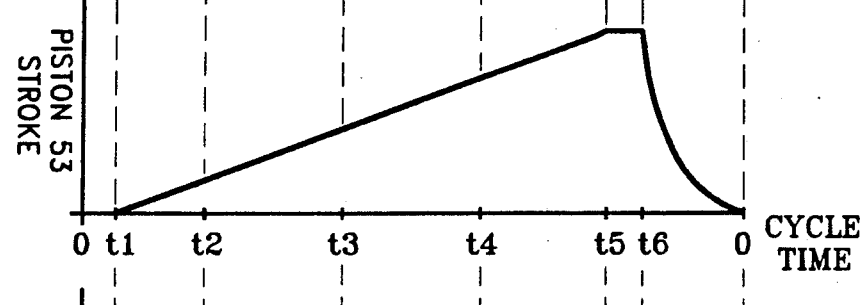
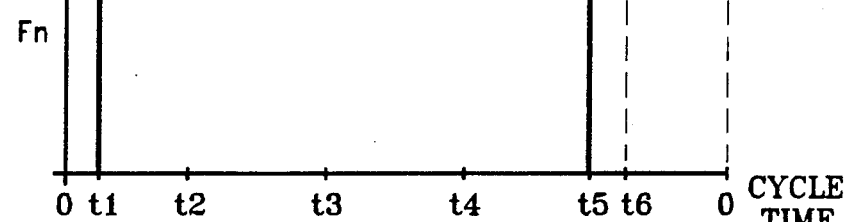
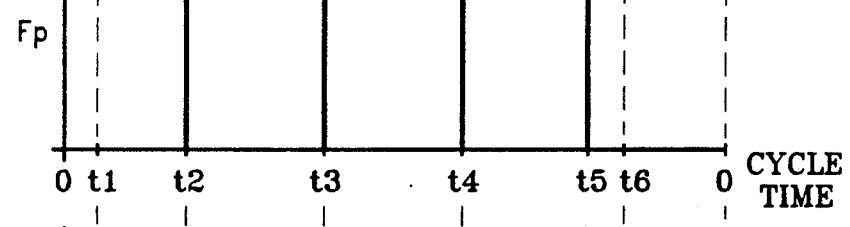
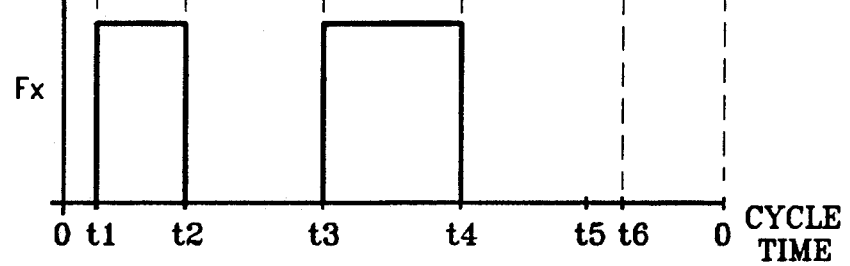
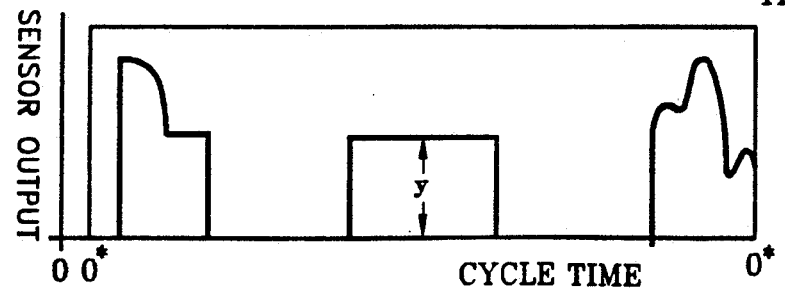

ANALYTIC APPPARATUS AND METHOD

This application is a continuation of application Ser. No. 07/094,734, filed July 7, 1987 and now abandoned.

FIELD OF THE INVENTION

This invention relates to a method and apparatus for analysis, especially analysis entailing the detection of substances in solution, for example direct analysis, reagent addition and known addition analysis, and titrimetry.

BACKGROUND ART

The automated detection and measurement of substances in solution has long been determined by a variety of known techniques which may be generally classified as either batch or flow analysis. In order that the advantages and novel aspects of the present invention be clearly understood, the essential features and limitations of the methods and means of the prior art will now be briefly described. A review of the field related to electrochemical analysis is provided by Feher, Zs; Nagy, G; Toth, K; Pungor, E. in CRC Crit. Rev. Anal. Chem. 1983. 14, 175-230 (hereinafter "Feher et al"). Descriptions of the prior art may also be found in standard textbooks such as "Instrumental Methods of Analysis", Sixth Edition, by Willard, Merritt, Dean and Settle, Wadworth Publishing Company, 1981.

1. BATCH TECHNIQUES (a) Automatic batch direct analysis

This relates to analysis where the sample is measured directly, without the addition of any other substance.

(b) Automatic batch reagent addition analysis It is intended for the purpose of this invention that the term "reagent addition analysis" refers to the addition of any solution to a fluid sample regardless of purpose, and includes:

(i) Simple reactions involving one reagent and the sample.
(ii) Complex and multistep reactions involving any number of reagents which may simultaneously or sequentially react with the sample.
(iii) The addition of solutions which do not react with the sample, but are added for a variety of purposes, for example, to enhance sensitivity, suppress interferences, fix reaction variables such as pH, ionic strength, clean the sensing system, or the like.
(iv) known addition, where a known volume of known concentration of the substance to be analyzed is added to a known volume of sample.

(c) Automatic batch titrimetry. This is described in Feher et al, at pages 175-188.

In general, batch techniques have the advantage of high accuracy with minimal sample carryover, but are complex mechanically, involving measurement of a known volume of sample, addition of reagent or titrant, mixing or transfer to a sensing system, washing of the sensing system after each analysis, etc. and are not well suited for on-line measurement Specific disadvantages of automatic batch titrimetry are:

(i) The volumetric accuracy of the sample is a limitation on the overall accuracy. Usually, a relatively large volume of sample is required so that the accuracy is not compromised. Typically, titrations are not performed on volumes of less than one milliliter of sample with any degree of accuracy.

(ii) The method is unsuitable for on-line measurement nor is the method suitable for measuring aliquots from a single sample.
(iii) The characteristics of the sensor, particularly the lag time, must be predetermined prior to titration and sufficient time must be allowed for sensor stabilization after each addition of titrant. This consideration imposes a limitation on the rate at which the titration can be performed without compromising accuracy.
(iv) The rate at which the titration can be performed is dependent on the rate at which the titrant and sample are mixed. As the volumes of sample are used are comparatively large, the mixing time, although small, becomes a significant limitation on the rate at which the titration can be performed without compromising accuracy.
(v) The method is unsuitable for slow reactions.
(vi) Automatic sampling is a complex procedure involving washing the sensor, stirrer and titrating vessel and dispensing new sample, which reduces sampling frequency.
(vii) The method is not well suited to an anaerobic measurement.

2. FLOW TECHNIQUES

For the purpose of this invention, a pump located before (that is, up-stream) from the point of sensing on a fluid flow line will be referred to as a "positive pump", whereas a pump located after (that is, down-stream) from the point of sensing on a fluid flow line will be referred to as a "negative" pump.

(d) Automatic flow direct Analysis

The sample may be propelled along a fluid line by a single positive pump or a single negative pump with provision for calibration, as described for example, in U.S. Pat. No. 3,556,950.

(e) Automatic flow reagent addition analysis

A number of techniques based on one or more positive pumps are known:

(i) Continuous stream analysis. Feher et al, page 216 is an example.
(ii) Segmented air space analysis. This is described in Feher et al, pages 191-200.
(iii) Flow injection analysis. This method and means are described by Ruzica, J., in "Flow Injection Analysis", John Wiley and Sons, 1981, in U.S. Pat. No. 4,002,2575, and in Feher et al, at pages 200-215.

(f) Automatic flow titrimetry

A number of techniques based on one or more positive pumps are known, as described in Feher et al, at pages 219-227:

(i) Continuous stream titrimetry;
(ii) Diluted sample or titrant gradient titrimetry;
(iii) Electrochemically generated titrant gradient titrimetry;
(iv) Diluted titrant gradient flow injection analysis.

Examples of continuous stream titrimetry are to be found in U.S. Pat. Nos. 2,977,199, 3,186,800, 3,192,017 and 4,120,657, in German patent specification 2031336, in French patent specification 2327543 and in European patent publication 159243.

Whilst the concept of flow based analysis offers the prospect of overcoming the limitations of batch analysis, the methods and means of the prior art relating to flow techniques (d), (e) and (f) have a number of common limitations:

(i) The limited flow accuracy of peristaltic pumps, which are commonly used in these techniques. This limits reproducibility, particularly with techniques (e) and (f). Peristaltic pumps also cause problems with certain detectors, for example, static electricity generated affects potentiometric detectors;

(ii) The various types of flexible tubing used in peristaltic pumps are not commonly compatible with organic solvents, thus restricting the type of solvent or number of analyses before replacement of the tubing is necessary;

(iii) Samples containing undissolved solids can block flow lines, or interfere with detectors, particularly with technique (e)(iii), which employs small bore flow lines.

In addition, flow techniques (e) and (f) have a number of specific limitations:

(iv) Techniques (e)(i) and (f)(i) are restricted to on-line analysis and are not suitable for analysis on small individual samples because of the dispersion of small samples in the flow line;

(v) Technique (e)(ii) cannot be used on-line against high or variable pressure, whereas (e)(iii) requires a complex injection system for on-line measurement;

(vi) Time based mixing of techniques (e)(ii and iii) limits the sampling frequency. Normally at least ten seconds is required per analysis;

(vii) Techniques (e)(ii and iii) suffer carryover from one sample to the next because of exponential tailing which limits accuracy, or reduces sampling frequency;

(viii) Techniques (e)(ii and iii) lack a quantitative relationship between injected sample and measured reaction product due to incomplete mixing. This requires a large range of standards for calibration and reduces sensitivity;

(ix) Certain detectors are unsuitable for (e)(ii and iii); for example, thermometric because of heat loss in long lengths of tubing;

(x) Technique (e)(ii) requires considerable time to set up for a particular analysis and is generally not suitable for short sample runs;

(xi) Techniques (f)(ii, iii and iv) require the preparation of titrant gradients prior to mixing with the sample, and are comparatively slow, requiring at least one minute per titration, with reproducibility limited to about 1%.

(xii) Technique (f)(iii) is limited to only a few titrants;

(xiii) Technique (f)(iv) has the same disadvantages as (e)(iii).

All of the methods and means of the prior art operate at fixed flow rates during measurement, with the exception of technique (f)(i).

In general, the automated techniques of the prior art utilize either separate pumps for delivering the sample and the titrant or reagent, or successive suction of both components with a syringe or like device.

DISCLOSURE OF THE INVENTION

The present invention seeks to provide a method and apparatus which permits flow analysis comparable in accuracy to batch techniques, and without at least some of the limitations of the aforementioned flow based techniques.

A principal object of the present invention is to enable direct analysis, reagent addition analysis or titrations to be performed on a sample without the need to measure the volume of the sample, and without the need to inject or pump the sample into the apparatus.

Another object of the present invention is to provide a method of analysis capable of application:

(a) Continuously on-line, against high or variable pressure;
(b) To individual samples; or
(c) To aliquots from a single sample.

The present invention entails the realization that substantial benefits in line with these objects can be achieved by utilizing a novel analytic arrangement in which control fluid such as reagent or titrant is both positively delivered past a fluid junction and positively drawn to a sensing position, by respective pumps which are operable at different and controllable rates of flow to cause aspiration of sample into the control fluid at the fluid junction.

The invention accordingly provides a method of analysis comprising:

delivering a first fluid to a sensing position at a controlled first rate of flow through a fluid junction;

simultaneously pumping fluid including said first fluid to the sensing position at a rate of flow greater than said first rate, whereby to aspirate further fluid into said first fluid at said fluid junction; and sensing a condition of the fluid at the sensing position.

The simultaneous pumping preferably comprises simultaneously drawing fluid to the sensing position. Preferably, the greater flow rate is held substantially constant while said first flow rate is controllably varied. The first and further fluid are advantageously positively mixed between the fluid junction and the position at which the condition is sensed.

Advantageously, the method further comprises confining the fluids to conduits and holding said flow rates equal for an interval before said delivery and drawing steps, whereby to flush the conduits with the first fluid.

Application to the method of titrimetry entails utilizing a titrant as said first fluid, continuously varying said flow rates until an end-point is sensed at the sensing location, and utilizing the then ratio between the flow rates to complete the analysis.

Application of the method to reagent addition analysis entails utilizing a reagent as said first fluid, and utilizing the ratio between the flow rates and the result of said sensing to complete the analysis.

The fluid may be a liquid, for example a solution.

Analytic apparatus according to the invention includes first and second pumps, a pair of ports for the first pump and at least one port for the second pump. A conduit provides fluid flow communication from a first of the ports of the first pump to a said one of the second pump. A fluid junction is disposed in said conduit, spaced from the said one port of the second pump, for admitting a further fluid to the conduit. A sensor is associated with the conduit to sense a condition of the fluid in the conduit, at least at a sensing position between the fluid junction and said one port of the second pump. The first and second pumps are respectively operable to deliver a first fluid to the conduit at a controllable first rate and to draw fluid from the conduit at a rate greater than said first rate, whereby to aspirate further fluid into the conduit at the fluid junction.

It will be appreciated that the first and second pumps respectively constitute positive and negative pumps, in the terminology used elsewhere in this specification.

The first pump is advantageously of piston-and-cylinder configuration, having a discontinuous flow cycle of operation including said delivery of the first fluid at said first rate, and a step in which the first fluid is not delivered to the conduit while the first pump is refilling.

Means is preferably disposed in the conduit between the fluid junction and the sensing position for mixing fluid in the conduit.

The apparatus preferably further comprises means operably coupled to the first pump for varying the flow rate of at least the first pump in accordance with a predetermined program. Respective valves advantageously control the ports, and means is provided for synchronizing the operation of both pumps and the valves.

The fluid junction is preferably a T-piece junction, but many alternatively be an aperture in the conduit for aspiration of the further fluid when the conduit is partially immersed therein. It should be noted that the term "T-piece" herein does not necessarily denote the actual shape or configuration of the fluid junction and is intended to include all fluid junctions where two or more inlet fluid streams unite and flow from a common outlet, regardless of shape or configuration.

BRIEF DESCRIPTION OF THE DRAWINGS

In order that the invention may be clearly understood and readily carried into effect, preferred embodiments and exemplary methods of operation, will now be described with reference to the accompanying drawings, in which:

FIG. 4, 5 and 6 are graphs of piston movement, flow rates and sensor output relating to particular analysis programs.

MODES FOR CARRYING OUT THE INVENTION

Figure 1:
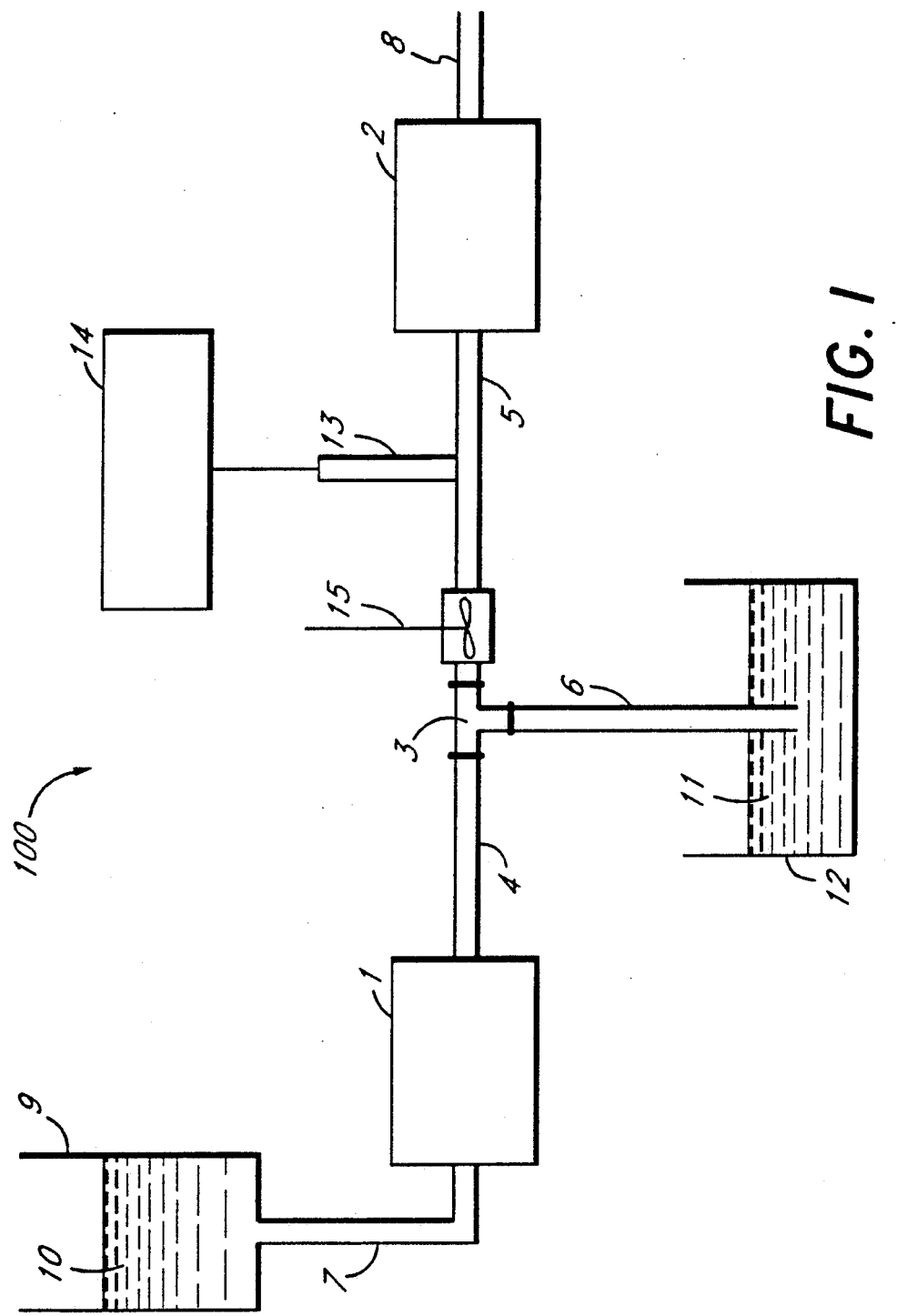
FIG. 1 is a combination block diagram of a basic configuration of analytic apparatus for carrying out the method of the invention where only one control solution is required to perform analyses.

The analytic apparatus or analyzer 100 illustrated schematically in FIG. 1 includes a positive pump 1 connected to reservoir 9 of solution 10 by means of fluid line 7. Negative pump 2 is connected to waste by waste fluid line 8. T-piece fluid junction 3 connected to positive pump 1 by positive fluid line 4, to negative pump 2 by negative fluid line 5, and to a container 12 of sample 11 by sample fluid line 6. Fluid lines 5, 6 with fluid junction 3 comprise conduit means providing fluid flow communication between the pumps. During normal analysis, the direction of flow is from positive pump 1 to negative pump 2. When the flow rate ($F_n$) of negative pump 2 is greater than the flow rate ($F_p$) of positive pump 1, sample 11 is drawn along sample fluid line 6 towards T-piece fluid junction 3, and thereby aspirated into negative fluid line 5 at junction 3, at a flow rate $F_x$. Mixer 15 uniformly mixes solution 10 and sample 11 in fluid line 5 prior to sensing a condition of the fluid in line 5 by a sensor 13, which outputs a signal to analyzer circuitry 14.

It is apparent that a large number of analytical programs may be generated by varying the ratio of $F_x:F_p$. It should be noted that it is possible to obtain any desired ratio of $F_x:F_p$ at any time in three ways:

(1) by holding $F_p$ constant and varying $F_n$;
(2) by holding $F_n$ constant and varying $F_p$;
(3) by varying both $F_p$ and $F_n$.

However, there are several advantages in employing option (2):

(i) The flow rate past sensor 13 is constant, which is desirable in the case where the sensor response is flow dependent;
(ii) The time taken for fluid to flow from the T-piece fluid junction 3 is constant, thus simplifying analysis, particularly on the case of a titration;
(iii) Different analytical programs can be generated by varying a single pump flow rate, that is, $F_p$, rather than the flow rates of both pumps.

In accordance with preferred option (2), positive pump 1 should have the following characteristics:

(a) pulse free, at least for the step of the cycle relating to measurement;
(b) Instantaneous response to programmed changes in flow rate (that is, not dampened);
(c) Highly reproducible flow rates for repeated cycling of analysis programs.

The preferred embodiment for positive pump 1 is a piston/cylinder pump with inlet and outlet valves so that a single forward stroke, during which measurement is made, and a single return stroke are completed within one cycle. Negative pump 2 may also be of this type, which permits accurate flow control and also backwashing in a manner to be described, but requires valves. Where product solutions may be dirty, or there is no requirement for high accuracy or backwashing, a pump such as a peristaltic pump may be preferred.

Figure 2A:
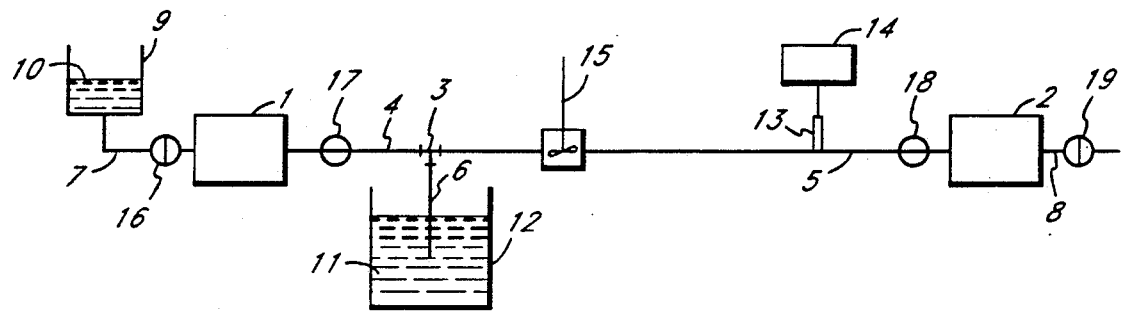
FIG. 2 diagrammatically depicts other configurations of analytic apparatus for performing the method of the invention, including cases where more than one control solution is required to perform analyses, and also showing possible variations in the position and nature of individual components.
Figure 2B:
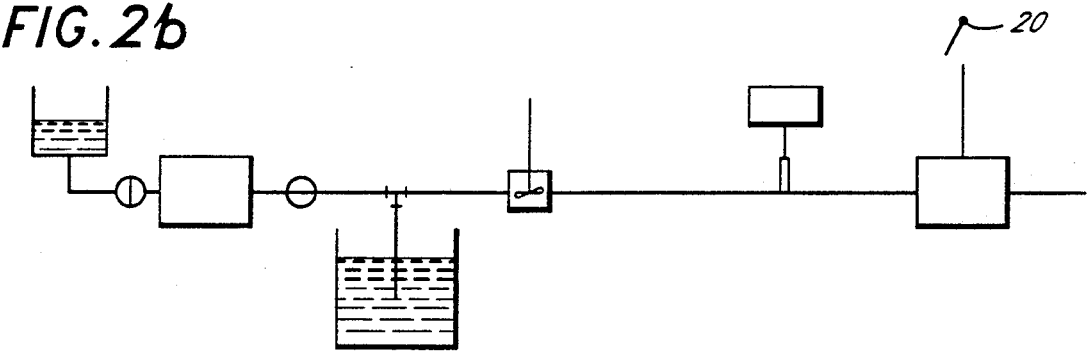
Figure 3:
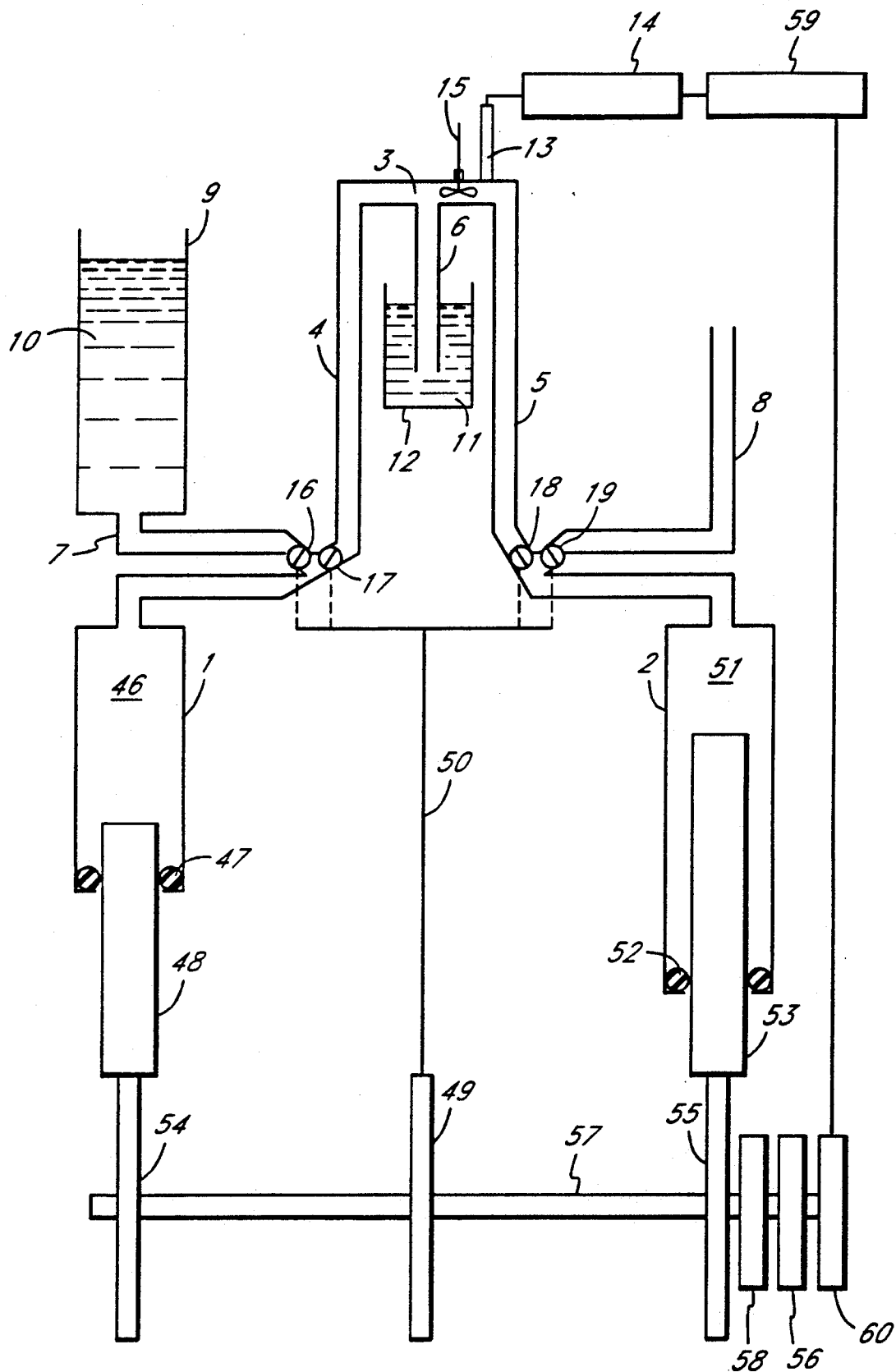
FIG. 3 is a somewhat diagrammatic cross-sectional view of apparatus in accordance with the invention, being a more detailed counterpart of the block diagram of FIG. 1.

Such an embodiment is depicted in FIG. 2a and further developed in FIG. 3. In FIG. 2a, positive pump 1 and negative pump 2 are piston/cylinder types, operating with solution valve 16, positive valve 17, negative valve 18 and waste valve 19. By synchronously opening or closing the four valves in conjunction with forward or reverse piston movement, two states exist per cycle:

(i) A flow state whereby sample 11 and/or sample solution 10 flow through negative fluid line 5, in order to perform measurement; and
(ii) A stopped flow state whereby sample and/or solution 10 do not flow through positive fluid line 4 and negative fluid line 5 in order to refill positive pump 1 with solution, and simultaneously expel reaction products, unreacted sample 11 or solution 10 to waste from negative pump 2 through waste fluid line 8.

It will thus be appreciated that the analyzer 100 has a discontinuous flow cycle of operation.

FIG. 3 depicts a cross-sectional, more developed view of the preferred embodiment of FIGS. 1 and 2a.

Positive pump 1 comprises cylinder 46, O-ring seal 47 and piston 48. Positive valve 17 and solution valve 16 may be mechanically operated by cam 49 in conjunction with connecting rod 50. Alternatively, valves 16 and 17 may be ball valves activated by changes in fluid pressure; solenoid valves activated by a switch, or a motor driven three way tap. Valves 16 and 17 operate in opposite stages (open or closed) depending on whether positive pump 1 is refilling with solution 10 or expelling solution 10 along positive fluid line 4.

Similarly, negative pump 2 comprises cylinder 51, O-ring seal 52 and piston 53. Alternatively to 0 ring seals, pistons 48 and 53 may terminate with slightly flexible fluid seals as in teflon syringes. Negative valve 18 and waste valve 19 operate synchronously with valves 16 and 17. The capacity of cylinder 51 is greater than that of cylinder 46. Piston 48 operates in two states: a forward stroke whereby piston 48 moves further into cylinder 46 and expels solution 10 contained within cylinder 46 along positive fluid line 4; or a reverse stroke whereby piston 48 withdraws from cylinder 46 and draws solution 10 into cylinder 46 from reservoir 9 along solution fluid line 7. Similarly piston 53 operates in two states: a forward stroke whereby piston 53 moves further into cylinder 51 and expels contents to waste through fluid line 8; or a reverse stroke whereby piston 53 withdraws from cylinder 51 and draws fluid (sample 11, solution 10 or reaction products) along negative fluid line 5 and into cylinder 53. Pistons 48 and 53 operate synchronously, but in opposite states, and in conjunction with valves 16, 17, 18 and 19. When solution valve 16 is closed positive valve 17 is open and piston 48 moves further into cylinder 46; at the same time negative valve 18 is open and waste valve 19 is closed and piston 53 withdraws from cylinder 51. The volume displaced by piston 53 in the reverse stroke is greater than that displaced in the same time interval by the forward stroke of piston 48 and the difference equals the volume of sample 11 aspirated into line 5. Conversely, when valve 16 is open, valve 17 is closed and piston 48 withdraws from cylinder 46; at the same time valve 18 is closed and valve 19 is open and piston 53 moves further into cylinder 51.

Fluid lines 4, 5 and 6 preferably comprise tubing of circular annular cross-section. The inside diameter is desirably as small as possible, to optimize sensitivity, but not so small as to be excessively susceptible to blockage. The inside diameter is preferably in the range 0.5 to 2.0 mm, most preferably in the range 1.0 to 1.5 mm. The length of each line is preferably as short as practicably possible, to reduce resistance to flow and to minimize sensing delays, but line 5 in particular must be of sufficient length between T-piece junction 3 and the effective sensing position to ensure adequate reaction with the analysis of interest (the "reaction zone"). This latter length is advantageously in the range 10 to 30 mm for most applications.

Displacement of pistons 48 and 53 may be achieved, and controlled, by, for example:
(1) Independently programmed linear actuators;
(2) Motors with independently programmed control;
(3) Cams profiled for particular analysis programs and linked by a common drive shaft.

Techniques (1) and (2) have program flexibility, but may not be synchronous under load, and are not suitable for very rapid cycle times. Technique (3) is exactly synchronous under load and easily suited to variable or rapid cycle times, but lacks flexibility, requiring different cams for different analysis programs. It may nevertheless be highly favorable e.g. for fixed installations.

FIG. 3 illustrates technique (3) and in particular utilizes a pair of cams 54, 55 on a shaft 56. Cams 54, 55 are constructed of a hard wearing, non-corroding material such as stainless steel. Using a device known as a "wire cutter", it is possible to cut cam profiles to any desired mathematical curve with very high precision. The piston displacement will be exactly reproducible from one cycle to the next. Cams 54 and 55 are attached to motor 56 by shaft 57. Motor 56 is a relatively high speed motor geared down to suitable cycle speeds by gearbox 58.

Attached to the shaft of motor 56 is encoder 60 which generates a larger, but fixed, number of pulses every cycle, regardless of cycle speed or variations of speed during the cycle. These pulses are synchronized to the output of sensor 13 via analyzer circuit 14 and are also recorded by timer 59, which may be used to interrupt the cycle. In this way, analyzer circuit 14 has direct knowledge at any moment of the cam positions and therefore of the flow rates ratio, which can be related to sample concentration, as described in subsequent examples.

Reverting now to FIG. 2, it is proposed to outline other configurations of apparatus for carrying out the invention. FIG. 2b shows a continuous flow type negative pump 2 which is not a piston/cylinder type and does not require valves 18 and 19. It operates in conjunction with piston/cylinder type positive pump 1, and may be stopped, when positive pump 1 refills, by switch 20.

Figure 2C:
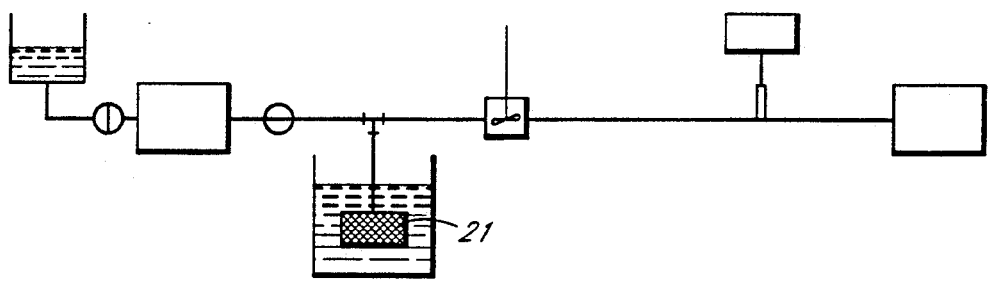

FIG. 2c shows a negative pump 2 which is a piston/cylinder type, but without valves 18 and 19, and waste line 8. This permits backwashing when positive pump 1, which is a piston/cylinder type, refills with solution 10. The contents of negative pump 2 are forced back along negative fluid line 5, along sample fluid line 6, through a filter 21 on the end of line 6 and into sample 11, thus dislodging particles which may have become embedded in filter 21 when sample 11 is drawn into sample fluid line 6. This process results in the contamination of sample 11, which is unimportant if only single measurement is to be performed on individual static samples. If more than one measurement is to be made on the one sample, sample fluid line 6 may be removed from container 12 during backwashing to prevent contamination. This is unnecessary if the sample is a flowing stream. Backwashing cannot be employed in cases where the reaction between solution 10 and sample 11 produces a precipitate.

Figure 2D:
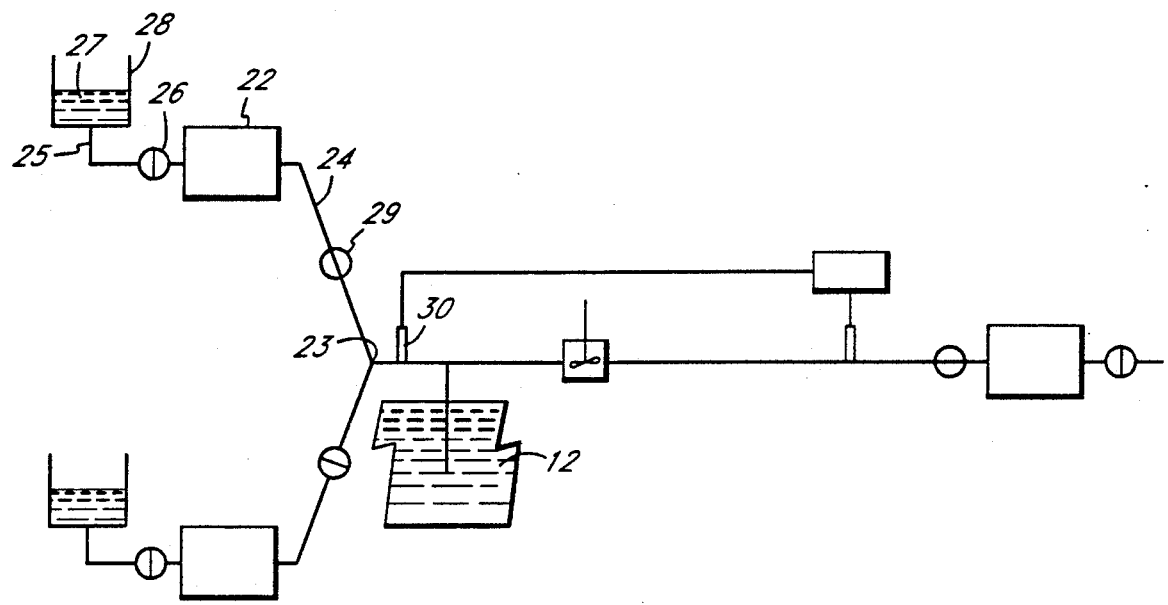

FIG. 2d illustrates a parallel positive pump configuration, where positive pumps 1 and 22 are connected to Y-piece fluid junction 23 by positive fluid lines 4 and 24 respectively, incorporating positive valves 17 and 29. Positive pump 22 is connected to reservoir 28 of solution 27 by solution fluid line 25 incorporating solution valve 26. This configuration may be operated as a dual flow system, where both positive pumps 1 and 22 operate at the same time, or as an "either/or" system where one or other pump operates. The former is useful when the reagent or titrant is unstable, and must be prepared from two components (solutions 10 and 27) before reaction with sample 11. The latter system is useful as a dual analysis or dual range option, where solutions 10 and 27 are different in composition or concentration. More than two positive pumps may be connected in parallel.

FIG. 2d also shows an alternate arrangement for the sensing system, which may be used in any of the configurations detailed. Sensor 13 is used in conjunction with a similar sensor 30 to form a differential sensor pair. Sensor 30 may be located on fluid line 4, as in FIG. 2d; on sample fluid line 6 as in FIG. 2e; or very close to sensor 13 on negative fluid line 5 as in FIG. 2f. The last mentioned arrangement produces an approximate first derivative output, which is useful in potentiometric titrations. FIG. 2d also shows sample 11 as a stream flowing through pipe 12 as an alternative to measurement in vessel 12.

Figure 2E:
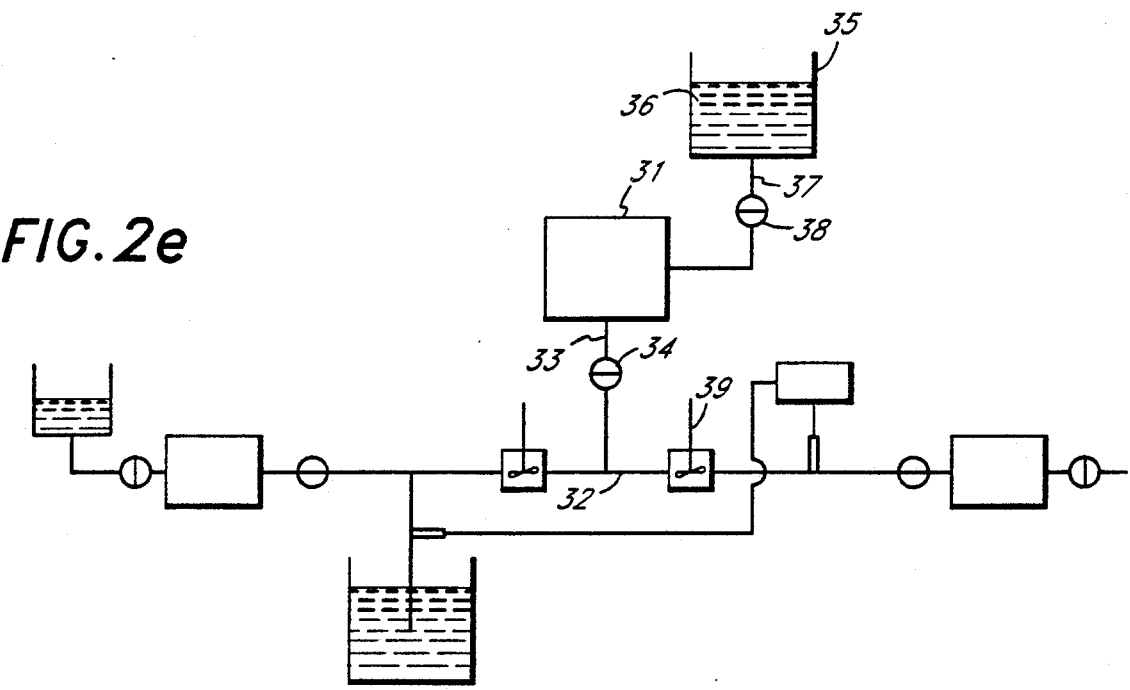

FIG. 2e illustrates a series positive pump configuration. Positive pump 31 is connected to T-piece fluid junction 32 by positive fluid line 33 incorporating positive valve 34; and to a reservoir 35 of solution 36 by solution fluid line 37 incorporating solution valve 38. Mixer 39 mixes solution with the reaction product resulting from the mixing sample 11 and solution 10. This configuration allows sequential analysis involving a number of solutions. More than two positive pumps may be connected in the series.

Figure 2F:
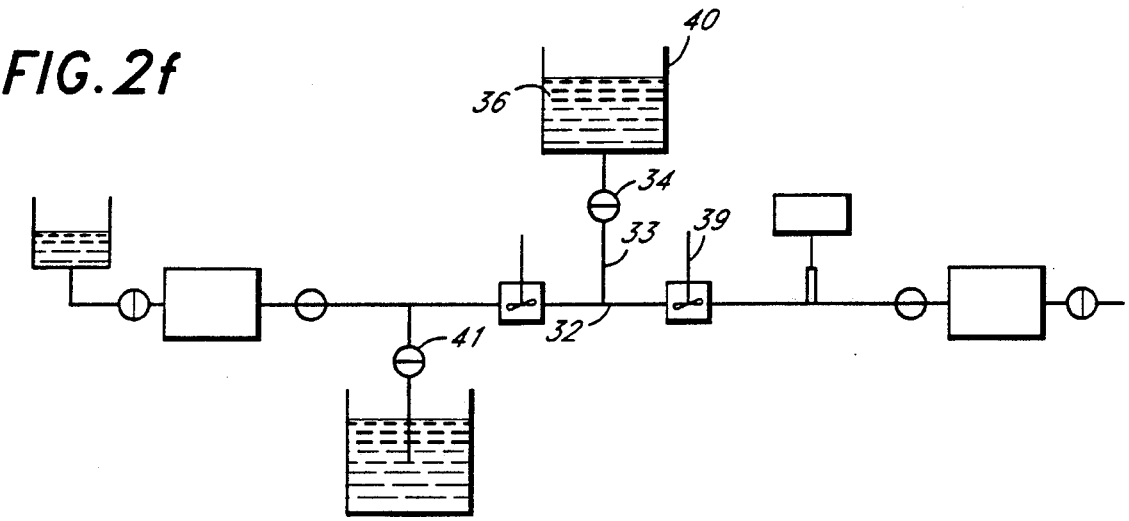

FIG. 2f is an alternative to FIG. 2e, whereby positive pump 31 is replaced by reservoir 40 of solution 36; and connected to T-piece fluid junction 32 by positive fluid line 33 incorporating positive valve 34. Sample valve 41 operates synchronously with positive valve 34, but in opposite state.

Figure 2G:
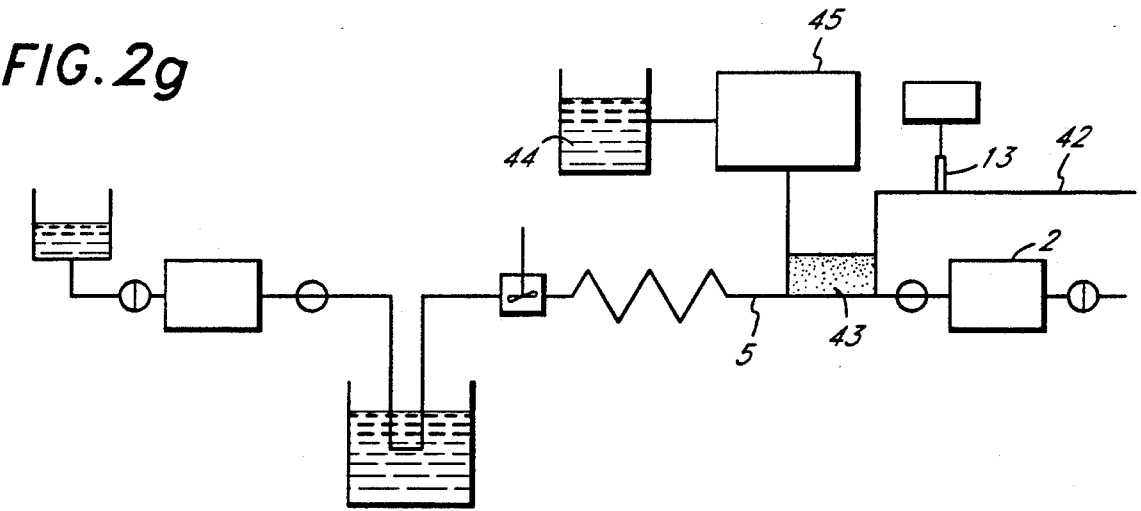

FIG. 2g illustrates a configuration where sample fluid line 6 has been removed. It will be noticed that positive fluid line 4 and negative fluid line 5 are immersed in sample 11, and T-piece fluid junction 3 becomes an aperture in the flow line through which sample 11 is drawn. The time taken for fluid to travel from mixer 15 to sensor 13 depends on the cycle speed and also the length of fluid line between mixer 15 and sensor 13. This length may be varied from very short, as in cases where the reaction between sample 11 and solution 10 is rapid, to relatively long, as in the case where the reaction between sample 11 and solution 10 is slow. The latter is schematically illustrated in FIG. 2g.

FIG. 2g also shows a configuration whereby sensor 13 is not located on negative fluid line 5, but on fluid pass line 42, so that the substance to be analyzed passed from fluid line 5 to fluid pass line 42 through a diffusion or dialysis membrane 43 without substantially affecting the volume of fluid drawn into negative pump 2. The substance to be analyzed then reacts with reagent 44 propelled along fluid pass line 42 propelled by pump 45 at a constant rate.

A typical analysis cycle consists of a number of steps, the number, nature, duration and order of which may be varied to suit particular analysis programs. The duration of each step can be characterized by a time interval, where the sum of the time intervals of all the steps of a cycle equals the cycle time.

The basic equation relating to flow rates involving a number of positive pumps of flow rates $F_p, \ldots F_z$; a single negative pump of flow rate $F_n$; and a sample flow rate $F_x$ is:

$$F_x = F_n - (F_p \ldots + F_z).$$

The optional steps include:
(a) Solution Flush $$F_n = F_p \ldots + F_z \neq 0; F_x = 0$$

No sample 11 is drawn into negative fluid line 5, and any sample 11 or reaction product is flushed from negative fluid line 5 and is replaced by solution 10. Sensor 13 records a base line after sample 11 or reaction product has cleared sensor 13.

(b) Sample Flush $$F_n > F_p \ldots + F_z \geq 0; F_x > 0$$

$F_x$ is chosen to be high so that the previous sample contained in sample fluid line 6 is replaced by the sample to be measured in a short time interval. Sample fluid line 6 is therefore primed with sample 11. This step is unnecessary with the configuration described in FIG. 2g.

(c) Sample Measurement $$F_n = F_x \neq 0; F_p \ldots + F_z = 0$$

No solution is drawn into negative fluid line 5. This step is used for direct analysis.

(d) Marker $$F_n > F_p \ldots + F_z \geq 0; F_x > 0$$

A relatively small volume of sample 11 is drawn into negative fluid line 5 in a very short time interval, thus sensor 13 records a sharp spike which may be used to mark the beginning of the following step. This step is useful for titrations, where the time interval from marker to endpoint is a measure of sample concentration, regardless of the position of sensor 13 in negative fluid line 5.

(e) Single Constant Addition for Reagent Addition Analysis $$F_n > F_p \ldots + F_z > 0; F_x > 0; \text{ and}$$

$$\frac{F_x}{F_p \ldots + F_z} = K \text{ (a constant)}$$

The value of K is chosen to suit a particular reaction and concentration range of samples. Sensor 13 records a step change where the height of the step (y), is related to the concentration of sample 11. The duration of the step should preferably be such that sufficient time is allowed for the stabilization of sensor 13, so that y may be an average value.

(f) Multiple Constant Addition

A sequence of step changes can be produced, which may be ascending or descending, by varying $$\frac{F_x}{F_p \ldots + F_z} = K \text{ (a constant)}$$

values, that is, $K_1, K_2, \ldots K_n$. Sensor records a sequence of step changes of heights y1, y2, ...yn, the difference which may be equal or unequal. Constant addition steps are used for reagent and known addition analysis.

(g) Single Gradient Formation for Simple Titrimetry or Reagent Addition Analysis $$F_n > F_p \ldots + F_z \geq 0; F_x \geq 0; \text{ and}$$

$$\frac{F_x}{F_p \ldots + F_z} = f(t),$$

where f(t) is any function of step time, for example, a linear or nonlinear function, and can be ascending or descending. The gradient may initiate and terminate with $$\frac{F_x}{F_p \ldots + F_z}$$

equal to:
(1) infinity, that is $F_p \ldots + F_z = 0$, or
(2) zero, that is $F_x = 0$, or
(3) $K_a$ (initiation constant) and $K_b$ (termination constant) which may be varied to suit particular ranges of sample concentrations. The ratio of the initial value to final value of $$\frac{F_x}{F_p \ldots + F_z}$$

determines the titration range.

(h) Multiple Gradient Formation for more complex titrimetry

A sequence of gradients can be produced by using more than one function;

$$\frac{F_x}{F_p \ldots + F_z} = f_1(t), f_2(t) \ldots f_n(t)$$

For example, $f_1(t) = f_2(t)$ produces an ascending/descending double titration symmetric about a midpoint. Gradients are used for titrations, and can also be used for reagent addition analysis.

(i) Stop $$F_n = F_p \ldots + F_z = F_x = 0$$

This step is useful for allowing a slow reaction time to complete or transfer of sample fluid line 6.

(j) Valve Change

Any of the valves described in FIGS. 2 and 3 may exist in an open or closed state and can be changed synchronously or independently with other valves.

(k) Refill

With positive and negative fluid lines closed by valves, positive pumps are refilled with solutions from solution reservoirs.

(l) Expel

With positive and negative fluid lines closed by valves, the contents of a piston type negative pump are expelled to waste. This occurs simultaneously with step (k).

(m) Transfer

With no flow of fluid taking place in positive fluid 4, and negative fluid line 5, as in steps (i), (k) and (l), sample fluid line 6 may be transferred to another sample.

(n) Backwash

With positive fluid line 4 closed and negative fluid line 5 open, the contents of negative piston type pump 2 are forced back along negative fluid line 5 as has been described.

The illustrated analytic configurations in accordance with the invention represent a significant advance over prior arrangements in that they not only share with known flow-based techniques the avoidance of accurately measuring volumes, but moreover avoid the need, common in prior flow based techniques, to positively inject or pump sample into the flow line. Provisions for injection are relatively complex and are susceptible to sample-to-sample contamination: the present arrangement, by utilizing a dual pump configuration to cause aspiration of sample, is comparatively simple, avoids contamination difficulties because of the ease of flushing, is very highly accurate, and permits the use of simple piston pumps in place of the previously favored but problematical peristaltic pumps.

The analytic technique of the invention is capable of handling very small sample volumes (i.e. less than 1 ml) at higher speeds and with higher reproducibility than has been previously achieved with flow-based methods. Air-segmented analysis is capable of an analysis every 20 seconds, flow injection analysis every 10 to 20 seconds: the inventive method can better 1 second per analysis depending on reactive time and sensor response. Even when changing over between analyses, the apparatus is susceptible to rapid changeover of sample and reagent. Reproducibility is found to be better than 0.1% for titrates and better than 1% for reagent addition analysis.

If positive mixing is included in the inventive technique, it is believed that a reproducible close quantitative relationship exists in reagent addition analyses between aspirated sample and measured reaction product. This enhances sensitivity and minimizes the need for a large range calibration standards, in contrast e.g. to air segmented analysis and flow injection analysis. Normally, only one or two standards are necessary.

The versatility of the inventive method will by now be apparent. It is applicable to continuous on-line applications, including against high or variable pressure, to individual samples, and to aliquots from single samples.

A further significant advantage of the inventive technique arises from the highly accurate flow rate control achievable with piston and cylinder pumps: it is possible to perform a titration within a very narrow flow rate range about an expected end point value. This facility enhances sensitivity and the possible fineness of the range is found to be smaller than with known flow based techniques.

The discontinuous cyclic operation of the inventive analyzer allows the incorporation, without operational disadvantage, of a very simple backwashing arrangement for flushing the sample life and clearing any associated filter.

Finally it is to be noted that the invention combines, in one technique, several features previously only attainable with either flow-based or batch techniques but not both. Notable among these features are lack of restriction on solvent and a wide choice of sensing systems (available with batch techniques) and applicability to anaerobic measurements, slow reactions, differential or derivative sensing with two sensors, and automatic compensation of sensor lag (all available with one or more prior flow-based techniques).

More particularly, as the apparatus can be constructed entirely of chemically inert materials such as stainless steel, glass, polypropylene or teflon, it is compatible with chemically aggressive solutions. Furthermore, complete mixing and short residence time in the fluid line 5 from mixer 15 to sensor 13, in the case of fast reactions, allows the use of thermometric detectors. The absence of electrostatic effects means that the method and means are suitable for potentiometric sensors. As the system is closed and not open to the atmosphere, anaerobic analysis is possible.

EXAMPLE 1

Of the infinite variety of analysis programs possible, a multiple constant reagent addition analysis involving steps $(j_1)$, (b), $(a_1)$, (f), $(a_2)$, $(j_2)$, (k,1) in order [utilizing the designations above] has been chosen as an example of an analysis program to be considered in detail in order to illustrate the working principle, and other examples of direct analysis and titrimetry will be considered more simply in terms of the steps already described.

Figure 4A:
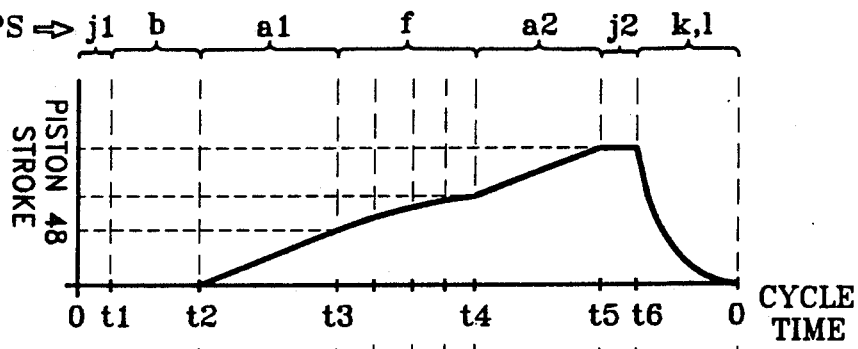
Figure 4B:
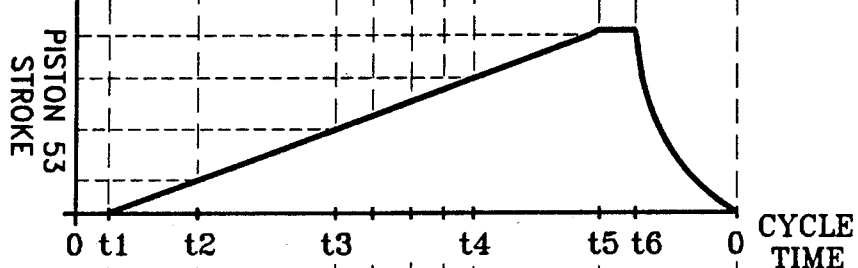
Figure 4C:
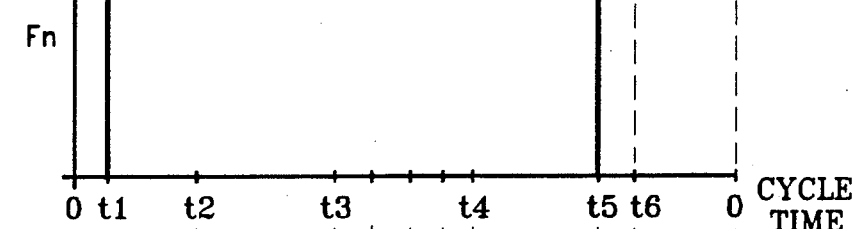
Figure 4D:
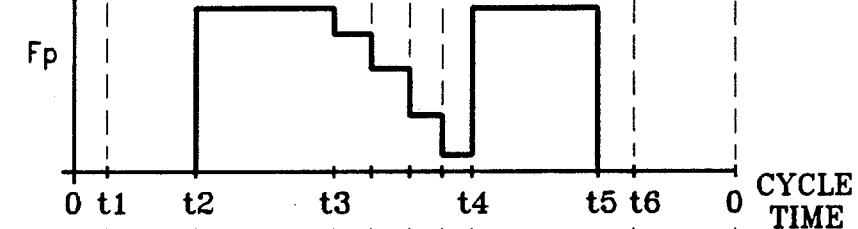
Figure 4E:
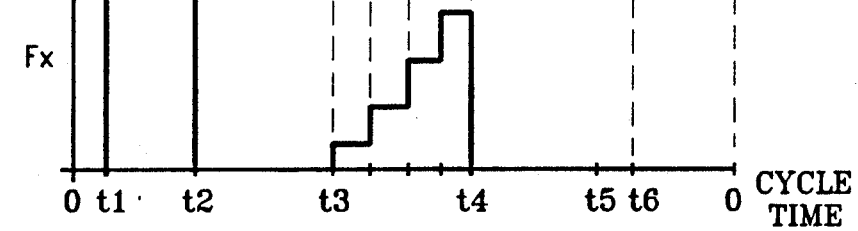
Figure 4F:
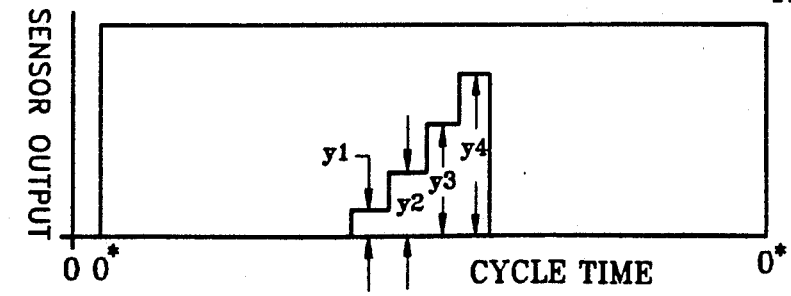
Figure 5A:
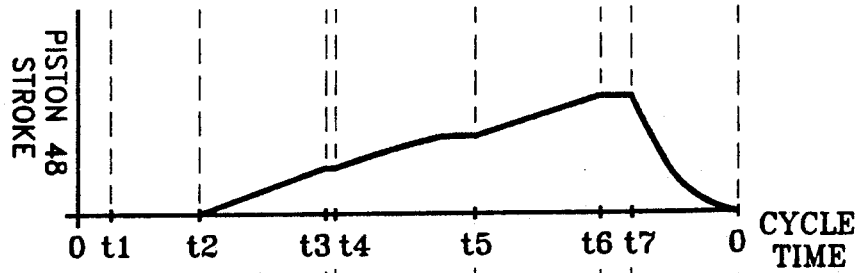
Figure 5B:
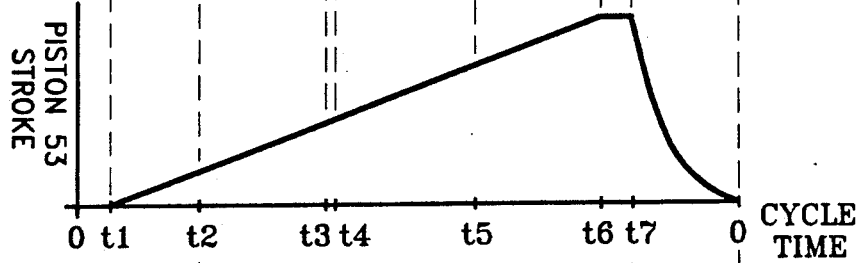
Figure 5C:
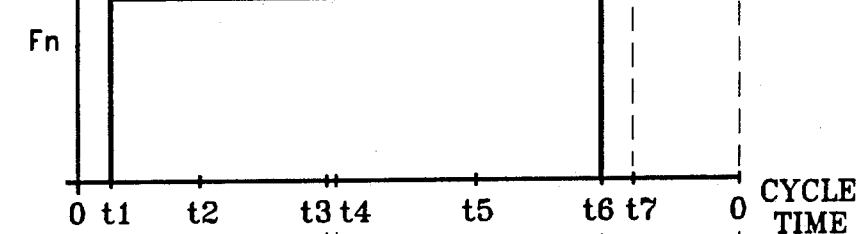
Figure 5D:
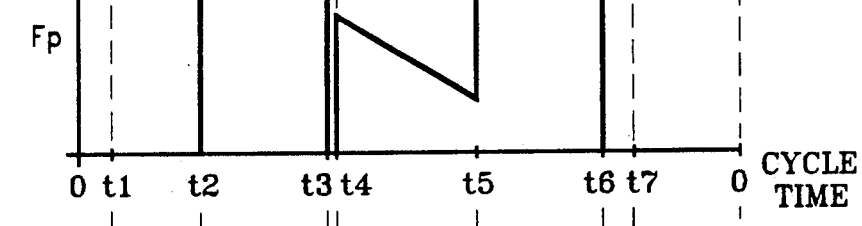
Figure 5E:
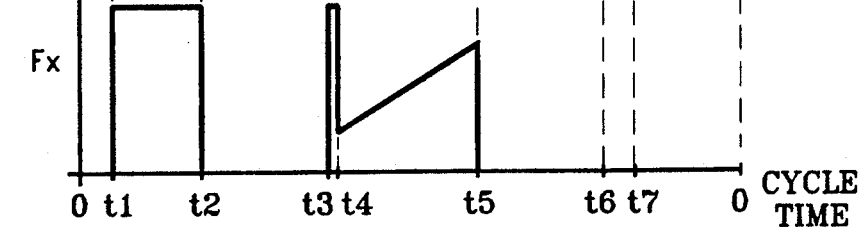
Figure 5F:
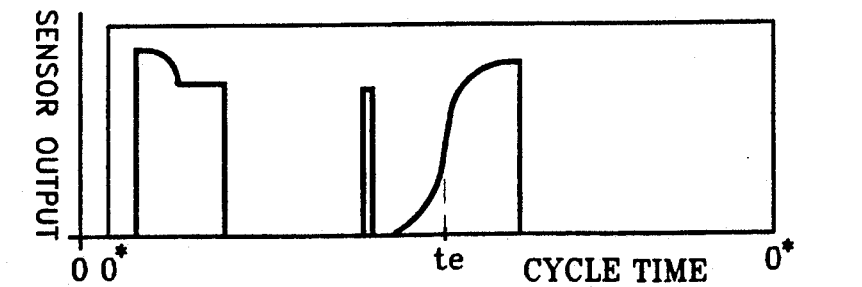

For this example, FIG. 4a shows piston 48 stroke length, FIG. 4b shows piston 53 stroke length, FIG. 4c plots $F_n$, FIG. 4d plots $F_p$, FIG. 4e plots $F_x$ and FIG. 4f shows sensor 13 output, all plotted as a function of cycle time on the same horizontal time axis where the time from point 0 (left-hand side) to point 0 (right hand side) represents one cycle. FIG. 4f is offset with respect to FIGS. 4a, b, c, d and e because of the time taken for fluid to travel from T-piece fluid junction 3 to sensor 13. This delay is represented by the time interval from time point 0 to time point 0*.

In order to illustrate the relationship between FIGS. 4a and 4b clearly, it will be assumed that the cross-sectional area of pistons 48 and 53 are equal, however, it will be understood that this is by no means essential. It will also be assumed for the purpose of this example, that sensor 13 measures a reaction product formed from reagent 10 and sample 11, and does not respond to either reagent 10 or sample 11.

The steps will now be detailed in turn:

Step ($j_1$)

In the time interval from 0 to $t_1$, valves 16 and 19 are closed and simultaneously valves 17 and 18 are opened. During the time interval from 0 to $t_1$, neither piston 48 nor piston 53 moves, thus avoiding pressure surges in fluid lines 4 and 5 as the valve changes take place.

Step (b)

With valves 16 and 19 closed and valves 17 and 18 open, piston 53 withdraws from cylinder 51 from position o to 1 in the time interval from $t_1$ to $t_2$, thus drawing fluid along fluid line 5 at a flow rate $F_n$. Also beginning at time $t_1$, piston 48 does not move in the same time interval from $t_1$ to $t_2$. Initially the previous sample contained in sample fluid line 6 is drawn into T-piece fluid junction 3 and along fluid line 6 by sample to be measured 11. As no reaction product is formed, sensor 13 records a base line. It is not necessary that $F_p$ be zero, but should be relatively small so that the sample flush is completed in minimal time.

Step ($a_1$)

With valves 16 and 19 closed and valves 17 and 18 open, piston 53 withdraws from cylinder 51 from position 1 to position m in the time interval from $t_2$ to $t_3$, thus drawing fluid along fluid line 5 at a rate $F_n$. Simultaneously piston 48 moves further into cylinder 46 from position o to position g in the time interval from $t_2$ to $t_3$, thus causing a flow of solution 10 (in this case a reagent) $F_p$ at a rate equal to $F_n$. Sample 11 does not flow along fluid line 6 but is contained in fluid line 6 up to T-piece fluid junction 3 and is flushed from fluid line 5, being replaced by solution 10. Thus sample fluid line 6 is primed with sample 11 to be analyzed, but no sample 11 is contained in fluid line 5. Analyzer 14 records a base line.

Step (f)

With valves 16 and 19 closed and valves 17 and 18 open, piston 53 withdraws from cylinder 51 from position m to position n in the time interval from $t_3$ to $t_4$, thus drawing fluid along fluid line 5 at a rate $F_n$. Simultaneously piston 48 moves further from cylinder 46 from position g to position h in the time interval from $t_3$ to $t_4$, thus causing a flow of reagent 10 along fluid line 4 at rates less than $F_n$. Sample 11 is aspirated into T-piece fluid junction 3 where it joins reagent 10, is mixed with reagent 10 by mixer 15 and flows past sensor 13 and thence to negative pump 2. By varying the ratio of $F_x/F_p$ in increments during the step, a stepped output of heights y1, y2, y3 and y4 is obtained. This affords information about the sensor response curve, and if this incremental differences (that is, y4−y3, y3−y2, and y2−y1) are unequal, profile matching between sample and standard improves accuracy. Any number of increments may be chosen; the number is primarily determined by the time taken for the sensor to stabilize. If the mixing is complete, a quantitative relationship exists between sample concentration and heights y1, Y2, y3 and y4.

Step ($a_2$)

With valves 16 and 19 closed and valves 17 and 18 open, piston 53 withdraws from cylinder 51 from position n to position p in the time interval from $t_4$ to $t_5$, thus drawing fluid along fluid line 5 at a rate $F_n$. Simultaneously piston 48 moves further into cylinder 46 from position h to position i in the time interval from $t_4$ to $t_5$, thus causing a flow of solution 10 at a rate of equal to $F_n$. Sample 11 does not flow along sample fluid line 6 and reaction product is flushed from fluid line 5, being replaced by solution 10. Analyzer 14 records a base line as before.

The time interval from $t_1$ to $t_5$ represents a complete forward stroke of piston 48 and a complete reserve stroke for piston 53, whereas time interval $t_6$ to $t_0$ represents a complete reverse stroke for piston 48 and a complete forward stroke for piston 53 so that both return to the initial starting position, that is, time point 0.

Step ($j_2$)

In the time interval from $t_5$ to $t_6$, valves 16 and 19 are opened and simultaneously valves 17 and 18 are closed. During the time interval from $t_5$ to $t_6$ neither piston 48 nor piston 53 moves, thus avoiding pressure surges in fluid lines 4 and 5 as the valve changes takes place.

Step (k,1)

With valves 16 and 19 open and valves 17 and 18 closed, piston 53 moves into cylinder 51 from position p to o in the time interval from $t_6$ to 0, thus expelling the contents along fluid line 8 to waste. Simultaneously, piston 48 withdraws from cylinder 46 from position i to position 0 in the time interval from $t_6$ to o, thus causing a flow of solution along fluid line 7 and into cylinder 46. No flow of solution 10 takes place in fluid lines 4 and 5, however, solution 10 is present in both lines. During this time, sample fluid line 6 may be transferred to another sample. The cycle then recommences.

To demonstrate the utility of the apparatus, the following analysis was performed. Iodide standards of 500 and 1000 micrograms per liter and low fat milk were separately aspirated into the apparatus and measured by known addition to a 1000 microgram per liter iodide standard in 0.01 M potassium chloride (the "reagent"), using a flow through cell (volume 10 microliters) containing an iodide ion selective electrode and single Ag-/AgCl/1M KCl reference electrode as sensor, and mixed by a micro reed (20 mm ×0.7 mm) vibrating at 20 hZ within a conduit of 1.6 mm I.D. The volume of solution aspirated and reagent consumed per cycle was found, from the characteristics and rate of displacement of the pumps, to be 0.9 ml for each, with a cycle time of 15 seconds, employing a two step constant addition where the ratio of solution aspirated to reagent was 60;40 and 40;60. Each measurement was repeated several times with a reproducibility of within 1% and the iodide in milk calculated to be 760 micrograms per liter from the two standards.

EXAMPLE 2

FIG. 5 illustrates a single gradient program with marker, comprising the following steps:

$(j_1)$, (b), $(a_1)$, (d), (g), $(a_2)$, $(j_2)$, (1, m)

and in this particular example, relates to a potentiometric titration for illustrative purposes only, viz, an acid-base titration with a conventional combination pH electrode as sensor. Step (b) shows the clearing of the previous sample which is replaced by the sample to be measured. Marker step (d) shows a sharp spike which defines the beginning of the titration. Gradient step (g) in this case shows a controlled linear decrease in $F_p$ and a linear increase in $F_x$, however the gradient need not be linear. The end-points occurs at time point $t_e$ and the time interval from marker to $t_e$ is a measure of sample concentration compensated for sensor lag, since any lag in sensor response will change both marker and endpoint by the same time interval. The titration range is determined by the ratio of $F_x/F_p$ [beginning of step (g)], to $F_x/F_p$ [termination of step (g)], and may be chosen to suit the variation of concentration in a particular group of samples.

A titrimetric analysis was performed as follows.

Standardized sodium hypochlorite solutions of 2.0, 2.5, 3.0, and 3.5 ppm chlorine, and chlorinated tap water were separately aspirated into the apparatus and titrated against $5 \times 10^{-5}$M iodide in pH 4.7 buffer, using a flow through cell (volume 10 microliters) containing an iodide ion selective electrode and single Ag/AgCl/1M KCl reference electrode as sensor, and mixed by a micro reed (20 mm ×0.7 mm) vibrating at 20 Hz within a conduit of 1.6 mm I.D. Again the volume of solution aspirated and titrant consumed was 0.9 ml for each, with a cycle time of 30 seconds, employing a single linear gradient and a titration range of 4. The end point was measured from a first derivative and the time taken from initiation to end-point measured accurately. Each measurement was repeated several times with a reproducibility within 0.1%, and total residual chlorine the tap water calculated to be 2.8 ppm from the standards.

EXAMPLE 3

FIG. 6 illustrates a direct analysis program with backwashing, comprising the steps:

$(j_1)$, (b), $(a_1)$, (c), $(a_2)$, $(j_2)$, (n)

Solution 10 in this case would normally be a standard of known concentration of the substance to be analyzed, which is recorded by sensor 13 as a base line in both steps (a). The height $y_x$ recorded by sensor 13 in step (c) is a measure of sample 11 concentration because solution 10 does not flow into fluid line 5 during this step. Valve change $(j_2)$ in this case only relates to valves 16 and 17. During backwashing step (n), the mixture of sample 11 and solution 10 contained in cylinder 51 is forced back along fluid line 5 and sample line 6. Sensor 13 records an irregular curve because the contents of cylinder 51 are not uniformly distributed within cylinder 51.

By way of more detailed example the pH of tap water was measured by aspirating 0.9 ml past a flow through cell containing a micro pH electrode and reference electrode (effective cell volume 50 microliters) within a thirty second cycle and comparing to a base line of NBS 6.88 phosphate buffer. The measured pH was 7.52 reproducible to better than 0.01 pH.

We claim:
1. An analytical apparatus comprising:
   first pump means including a pair of ports for delivering a reagent fluid at a fluid flow rate;
   a fluid junction for admitting sample fluid;
   first conduit means providing fluid flow communication from a first of said ports of said first pump means to said fluid junction;
   second pump means including at least one port for drawing fluid to be sensed at a second flow rate from said fluid junction to a sensing position and thence to said at least one port of said second pump means;
   second conduit means providing fluid flow communication from said fluid junction to said at least one port of said second pump means;
   means to mix said fluid to be sensed between said fluid junction and said sensing position to form mixed fluid;
   sensor means responsive to a fluid condition in at least said second conduit means to sense a condition of said mixed fluid at said sensing position between said fluid junction and said at least one port of the second pump means; and
   flow rate control means operably coupled to at least one of said first pump means and said second pump means for controllably varying the flow rate of at least said one pump means in order to produce a plurality of ratios of said first and second flow rates in accordance with a sequence of functional steps, each of which steps is defined by at least one of a distinct flow rate ratio, a series of distinct flow ratios, a distinct gradient of flow rate ratios, or a series of distinct gradients of flow rate ratios, said steps including at least one step wherein said second flow rate is greater than said first flow rate and sample fluid is thereby aspirated at said fluid junction and drawn to said sensing position;
   wherein said analysis of said sample fluid is determined by the relationship of the conditions of said mixed fluid at the sensing position for said plurality of ratios of said first and second flow rates; and
   wherein the condition of said mixed fluid analyzed at the sensing position is determined by the ratio of said first and second flow rates.

2. The analytical apparatus according to claim 1 wherein said first pump means is of piston-and-cylinder configuration, having a discontinuous flow cycle of operation including delivery of the first fluid at said first rate, and a step in which the first fluid is not delivered to the first conduit means while the first pump means is refilling.

3. The analytical apparatus according to claim 1 wherein said means to mix further includes a mixing device disposed in said second conduit means between the fluid junction and said sensing position.

4. The analytical apparatus according to claim 1 wherein said flow rate control means is operably coupled to said first pump means for controllably varying the flow rate only of the first pump means.

5. The analytical apparatus according to claim 1 further comprising respective valves controlling said pair of ports and said at least one means for synchronizing the operation of said first and second means and said valves.

6. The analytical apparatus according to claim 1 wherein said fluid junction is a T-piece junction.

7. The analytical apparatus according to claim 1 wherein said fluid junction is an aperture in said second conduit means for aspiration of said sample fluid when the second conduit means is partially immersed therein.

8. The analytical apparatus according to claim 1 wherein said sensor means is arranged for sensing a condition of fluid in the second conduit means at two close-spaced sensing positions.

9. The analytical apparatus according to claim 1 wherein said sensor means is so positioned in said first and second conduit means that is senses a condition of fluid in the first and second conduit means to either side of the fluid junction.

10. The analytical apparatus according to claim 1 wherein said second pump means is of piston-and-cylinder configuration having a discontinuous flow cycle of operation including a step at which said mixed fluid is drawn at said second flow rate, and a step in which the said mixed fluid is not drawn through said conduit means while the second pump means is expelling.

11. The analytical apparatus according to claim 1 further comprising a receptacle for said reagent fluid, coupled for fluid delivery to the second of said pair of ports of the first pump means.

12. The analytical apparatus according to claim 1 further comprising electronic means coupled to the sensor means and to said first and second pump means for analyzing the mixture of the reagent and sample fluids as a function of flow ratio, and outputting an analytic value.

13. The analytical apparatus according to claim 1 further including at least one additional pump means having an outlet port coupled to said first conduit means parallel to said first pump means, for delivering a respective additional fluid to the first conduit means.

14. The analytical apparatus according to claim 1 further comprising a filter in said second conduit means at or adjacent said fluid junction, which filter is traversed by said sample fluid which has been aspirated and is cleanable by backwashed fluid delivered by said second pump means by reverse operation thereof.

15. The analytical apparatus according to claim 1 wherein said flow rate control means produces non-incremental, substantially pulse free operation of said first and second pump means.

16. The analytical apparatus according to claim 1 wherein said flow rate control means comprises a cam means for controlling operation of said first and second pump means.

17. The analytical apparatus according to claim 1 wherein said flow rate control means comprises a DC or AC motor means for controlling operation of said first and second pump means.

18. The analytical apparatus according to claim 1 wherein said flow rate control means is varied in accordance with dynamic control from said sensor means.

19. The analytical apparatus according to claim 1 wherein said sensor means is suitable for at least one of direct analysis, reagent addition analysis and titrimetry.

20. The analytical apparatus according to claim 1 wherein said sensor means further comprises a subsidiary conduit and subsidiary pump means and a sensor connected at said sensing position in order to transport fluid or components thereof to a further sensing position.

21. The analytical apparatus according to claim 1 wherein said plurality of ratios includes a plurality of distinct ratios of said first and second flow rates at which said sample fluid is aspirated at said fluid junction and then to said sensing position, the analysis of said sample fluid being determined by the relationship of the condition of fluids at the sensing position for said plurality of flow rate ratios at which said sample fluid is aspirated.

22. The apparatus according to claim 21 wherein said flow rate control means is arranged whereby the ratio of said first and second flow rates at which said sample fluid is aspirated is adjustable to plurality of distinct values.

23. A method of analysis comprising:
delivering a reagent fluid to a fluid junction at a first flow rate;
simultaneously drawing a fluid to be sensed from said fluid junction to a sensing position at a second flow rate;
controllably varying at least one of said first flow rate and second flow rate in order to produce a plurality of ratios of said first flow rate and second flow rate in accordance with a sequence of functional steps, each of which steps is defined by at least one of a distinct flow rate ratio, a series of distinct flow rate ratios, a distinct gradient of flow rate ratios, or a series of distinct gradients of flow rate ratios, said steps including at least one step wherein second flow rate is greater than said first flow rate and sample fluid is thereby aspirated at said fluid junction and included as a component of said fluid to be sensed as it is drawn to said sensing position;
mixing said sample fluid to be sensed with said reagent fluid between said fluid junction and said sensing position to form mixed fluid;
sensing a condition of the mixed fluid at the sensing position in order to perform analysis of said sample fluid;
wherein said analysis of said sample fluid is determined by the relationship of the conditions of said mixed fluid at the sensing position for said plurality of ratios of said first and second flow rates; and
wherein the condition of said mixed fluid analyzed at the sensing position is determined by the ratio of said first and second flow rates.

24. The method according to claim 23 wherein said second flow rate is held substantially constant while said first flow rate is controllably varied.

25. The method according to claim 23 further comprising confining said sample and reagent fluids to conduits and wherein a further of said steps comprises holding said first flow rate and said second flow rate equal for an interval before said delivery step and said drawing step, whereby to flush the conduits with said reagent fluid.

26. The method according to claim 23 further comprising confining said sample and reagent fluids to conduits and wherein a further of said steps comprises holding said first flow rate at zero for an interval, whereby to flush the conduits with said sample fluid.

27. The method of analysis according to claim 23 comprising a method of titrimetry which includes utilizing a titrant as said reagent fluid, continuously varying said first flow rate and said second flow rate until an end-point is sensed at the sensing position and utilizing the ratio of said first flow rate and second flow rate at a said end-point to complete the analysis.

28. The method according to claim 23 wherein said reagent fluid and said sample fluid are liquids.

29. The method according to claim 23 wherein said analysis is a direct analysis or a reagent addition analysis or a titration.

30. The method according to claim 23 said plurality of ratios includes a plurality of distinct ratio of said first and second flow rates at which said sample fluid is aspirated at said fluid junction and then to said sensing position, the analysis of said sample fluid being determined by the relationship of the condition of the mixed fluid at the sensing position for said plurality of flow rate ratios at which said sample fluid is aspirated.

31. The method according to claim 30 wherein the ratio of said first and second flow rates at which said sample fluid is aspirated is adjustable to a plurality of distinct values.

* * * * *